(12) United States Patent
Pekar

(10) Patent No.: US 6,978,784 B2
(45) Date of Patent: Dec. 27, 2005

(54) ATRAUMATIC ENDOTRACHEAL TUBE INTRODUCER AND ATRAUMATIC INTUBATION METHODS

(75) Inventor: Alexandr Pekar, Brooklyn, NY (US)

(73) Assignee: The Research Foundation State University of New York, Albany, NY (US)

( * ) Notice: Subject to any disclaimer, the term of this patent is extended or adjusted under 35 U.S.C. 154(b) by 23 days.

(21) Appl. No.: 10/733,906

(22) Filed: Dec. 11, 2003

(65) Prior Publication Data

US 2005/0126564 A1 Jun. 16, 2005

(51) Int. Cl.[7] ............................................. A61M 16/00
(52) U.S. Cl. ......................... 128/207.14; 128/207.15; 128/207.18; 128/200.26; 600/120; 600/121
(58) Field of Search ..................... 128/207.14, 207.15, 128/207.16, 207.18, 200.26; 600/120, 121, 600/124, 125

(56) References Cited

U.S. PATENT DOCUMENTS

| | | | |
|---|---|---|---|
| 4,502,482 A | | 3/1985 | DeLuccia et al. |
| 4,612,927 A | * | 9/1986 | Kruger .................. 128/200.26 |
| 4,773,394 A | * | 9/1988 | Reichstein et al. ......... 600/114 |
| 5,496,259 A | * | 3/1996 | Perkins ........................ 600/124 |
| 5,749,357 A | * | 5/1998 | Linder .................. 128/200.26 |
| 5,873,362 A | | 2/1999 | Parker |
| 5,876,329 A | * | 3/1999 | Harhen ........................ 600/125 |
| 5,919,183 A | | 7/1999 | Field |
| 6,146,402 A | | 11/2000 | Munoz |
| 6,257,236 B1 | | 7/2001 | Dutkiewicz |
| 6,432,042 B1 | | 8/2002 | Bashour |
| 6,508,757 B1 | * | 1/2003 | Song et al. ................. 600/120 |
| 6,749,601 B2 | * | 6/2004 | Chin ............................. 606/1 |
| 2005/0049460 A1 | * | 3/2005 | Mikkaichi et al. .......... 600/121 |

FOREIGN PATENT DOCUMENTS

WO WO 90/06077 * 6/1990 ............ A61B 1/06

* cited by examiner

Primary Examiner—Henry Bennett
Assistant Examiner—Amanda Wieker
(74) Attorney, Agent, or Firm—Sander Rabin

(57) ABSTRACT

An endotracheal tube introducer ("introducer") that slides within an endotracheal tube. The introducer has a tubular wall that defines a lumen extending between a split proximal end and a distal end of the introducer. The tubular wall has an outer diameter that is less than an inner diameter of the endotracheal tube. The tubular wall is circumscribed by an invertible shroud. The invertible shroud flexes distal-ward ("forward") proximal-ward ("rearward"). The proximal end of the introducer is introduced into a distal end of the endotracheal tube and the shroud is manually retroflexed rearward to cover the sharp margins of the end of the endotracheal tube prior to its insertion into a patient's airway. After the endotracheal tube has been properly positioned, the introducer is withdrawn, the motion of its withdrawal anteflexing the shroud forward for removal through the endotracheal tube.

5 Claims, 19 Drawing Sheets

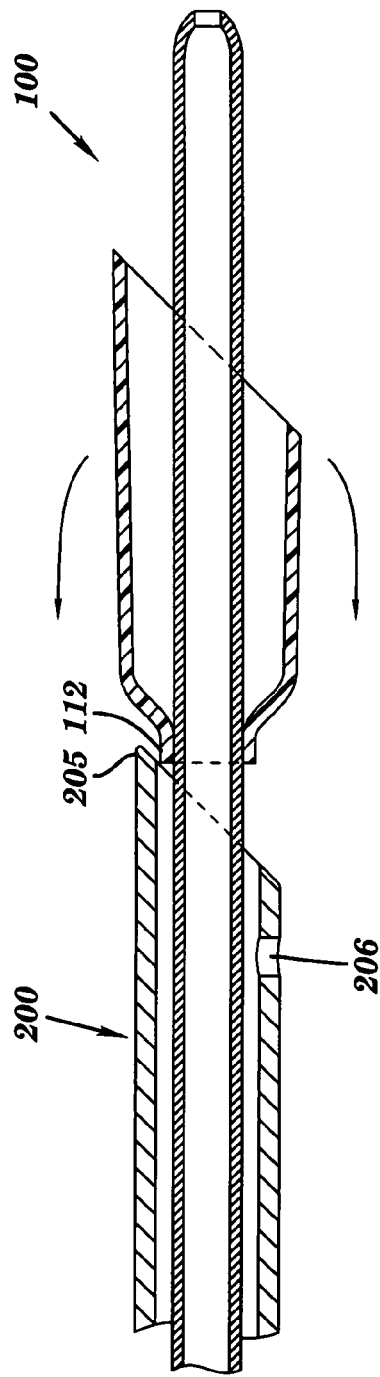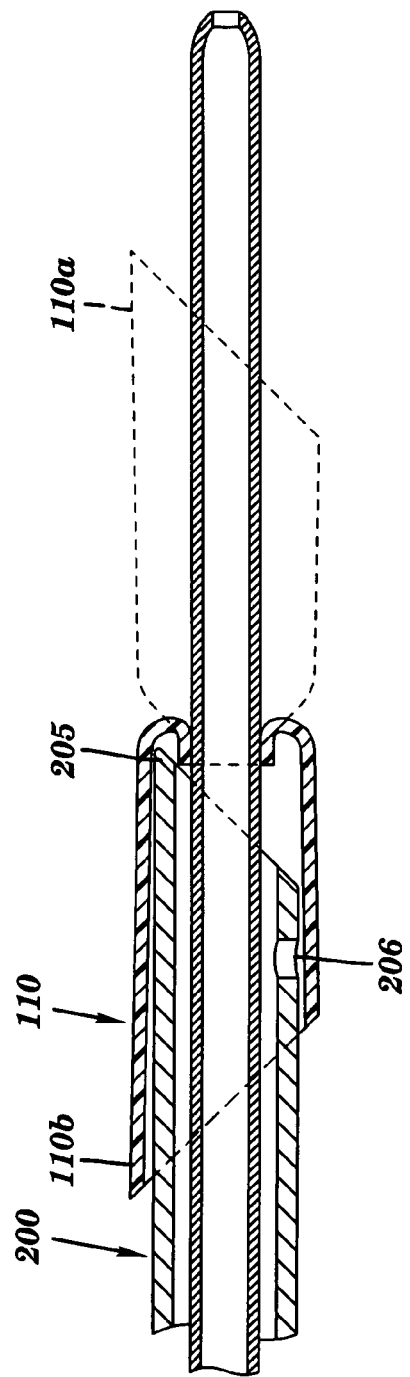
FIG. 7B
FIG. 7C

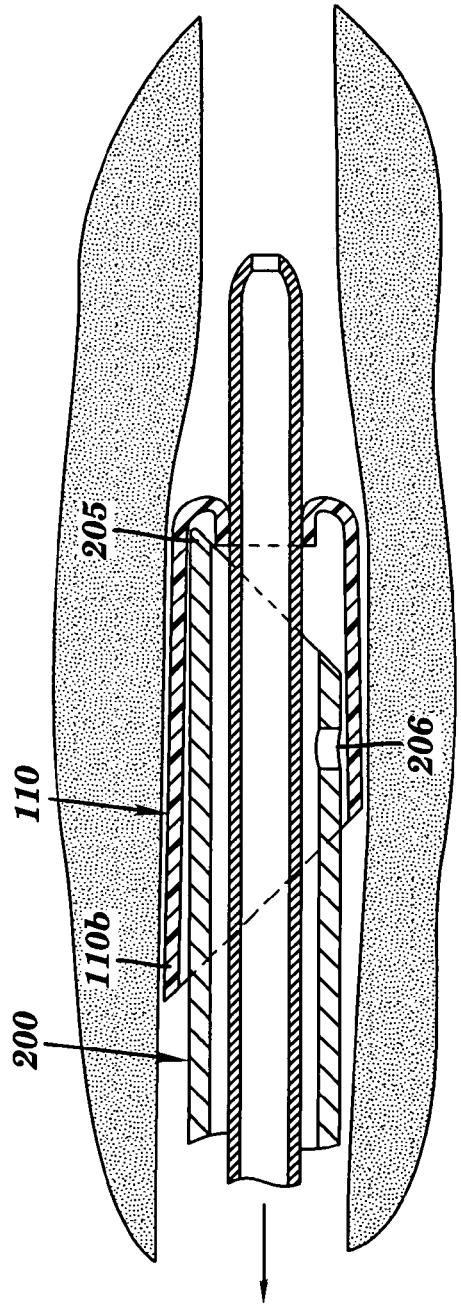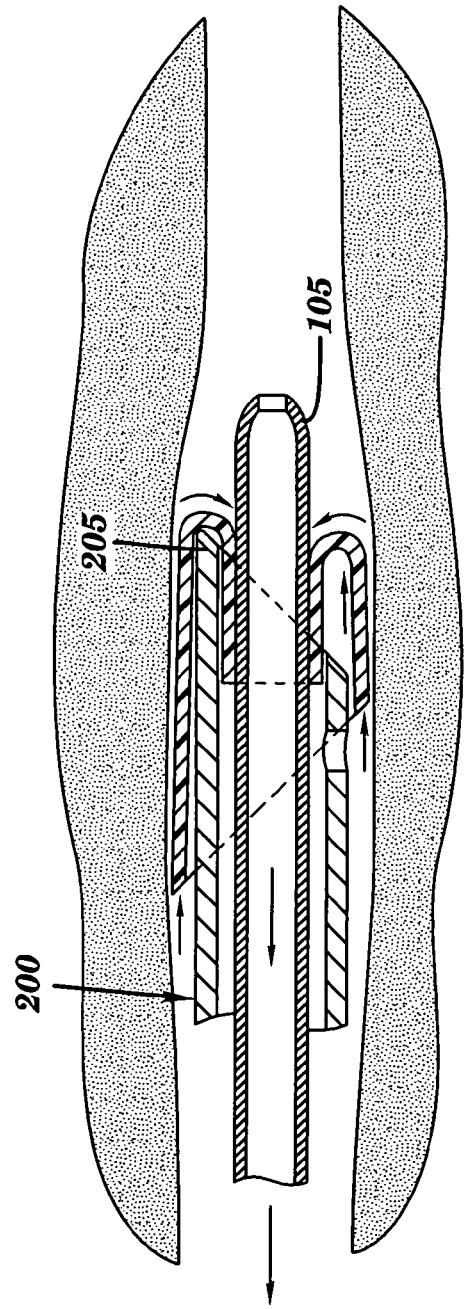

ATRAUMATIC ENDOTRACHEAL TUBE INTRODUCER AND ATRAUMATIC INTUBATION METHODS

BACKGROUND OF THE INVENTION

1. Technical Field

The present invention pertains to the field of endotracheal intubation.

2. Related Art

Endotracheal intubation is a procedure for creating an artificial airway in a patient by inserting an endotracheal tube ("ETT") into a patient's trachea through the patient's nose or mouth.

Fiberoptic endotracheal intubation is an intubation technique that utilizes a fiberoptic endoscope ("fiberscope") to facilitate the proper placement or exchange of an ETT. A health care provider, using the direct visualization provided by the eyepiece of the fiberscope, directs the fiberscope, with an ETT pre-loaded ("piggy-backed") on the fiberscope's insertion cord, into a patient's trachea. Using the fiberscope as a guide wire, a distal tip of the ETT is then advanced over the fiberscope into the trachea between and beyond the vocal cords.

In an endotracheal tube exchange, an in-place ETT in a patient is withdrawn over a tube exchanger that serves as a guide wire for its removal, and a fresh ETT is thereafter inserted into the patient's airway, by advancement over the tube exchanger, so that its distal tip passes between and beyond the vocal cords.

When an ETT is advanced over the fiberscope or a tube exchanger, the distal tip of the ETT may impinge on the glottis, the epiglottis, the larynx, or other anatomy of the airway, causing trauma and resisting further advancement into the trachea. The impingement of the ETT on the glottis, the epiglottis or the larynx has been attributed to a cleft that arises between the outer ETT that is concentric with either the inner guiding fiberscope or the inner guiding tube exchanger, over which the ETT rides. As the ETT is advanced along the fiberscope or tube exchanger, the cleft between them also advances, with a propensity for snaring tissues lying in its path.

The present invention minimizes the risk of trauma to tissues in the course of fiberoptic intubation and ETT exchange by covering the offending cleft with an a traumatic, flexible shroud.

The present invention also protects the vocal cords from trauma as the ETT is passed between them, particularly when vocal cord edema or mild stenosis is present, in both fiberoptic intubation and intubation performed with or without a laryngoscope to facilitate placement or exchange of an ETT.

The present invention additionally offers advantages in both fiberoptic intubation and intubation performed with or without a laryngoscope to facilitate placement or exchange of an ETT, because of a streamlining effect created by the shroud that facilitates smooth insertion of the ETT. This advantage is especially important in difficult intubations when airway visibility is poor or when the opening between vocal cords through which the ETT must pass is very small.

SUMMARY OF THE INVENTION

The invention comprises a flexible endotracheal tube introducer ("introducer") for slidably removable disposition within an endotracheal tube ("ETT"), said introducer having a wall defining a lumen extending between a split proximal end and a distal end of said introducer, said wall having an outer diameter that is less than an inner diameter of said ETT, and said wall being circumscribed by an invertible shroud for distal-ward ("forward") flexion and proximal-ward ("rearward") flexion.

BRIEF DESCRIPTION OF THE DRAWINGS

FIG. 7B is a schematic illustration showing a flexible endotracheal tube introducer advanced into an endotracheal tube so that a ring of the flexible endotracheal tube introducer apposes a beveled distal tip of the endotracheal tube.

FIG. 7C is a schematic illustration showing a shroud of a flexible endotracheal tube introducer flexed from its anteflexed, forward or distal-ward conformation to its retroflexed, rearward or proximal-ward conformation to cover a beveled tip and Murphy eye of an endotracheal tube.

FIG. 7D-1 is a schematic illustration showing a proximal end of a flexible endotracheal tube introducer fixed to a proximal end of an endotracheal tube using a fixation ring, thereby forming a combined endotracheal tube introducer-endotracheal tube unit.

FIG. 7D-2 is a schematic illustration showing a proximal end of a flexible endotracheal tube introducer fixed to a proximal end of an endotracheal tube using surgical tape, thereby forming a combined endotracheal tube introducer-endotracheal tube unit.

FIG. 7F is a schematic illustration showing a shroud of a flexible endotracheal tube introducer in its retro-flexed or proximal-ward position to cover a beveled tip and Murphy eye of an endotracheal tube, about to be withdrawn from an endotracheal tube.

FIG. 7G is a schematic illustration showing a shroud of a flexible endotracheal tube introducer in the process of being its anteflexed to its forward or distal-ward conformation as it is being withdrawn from an endotracheal tube.

DETAILED DESCRIPTION OF THE INVENTION

Figure 1:
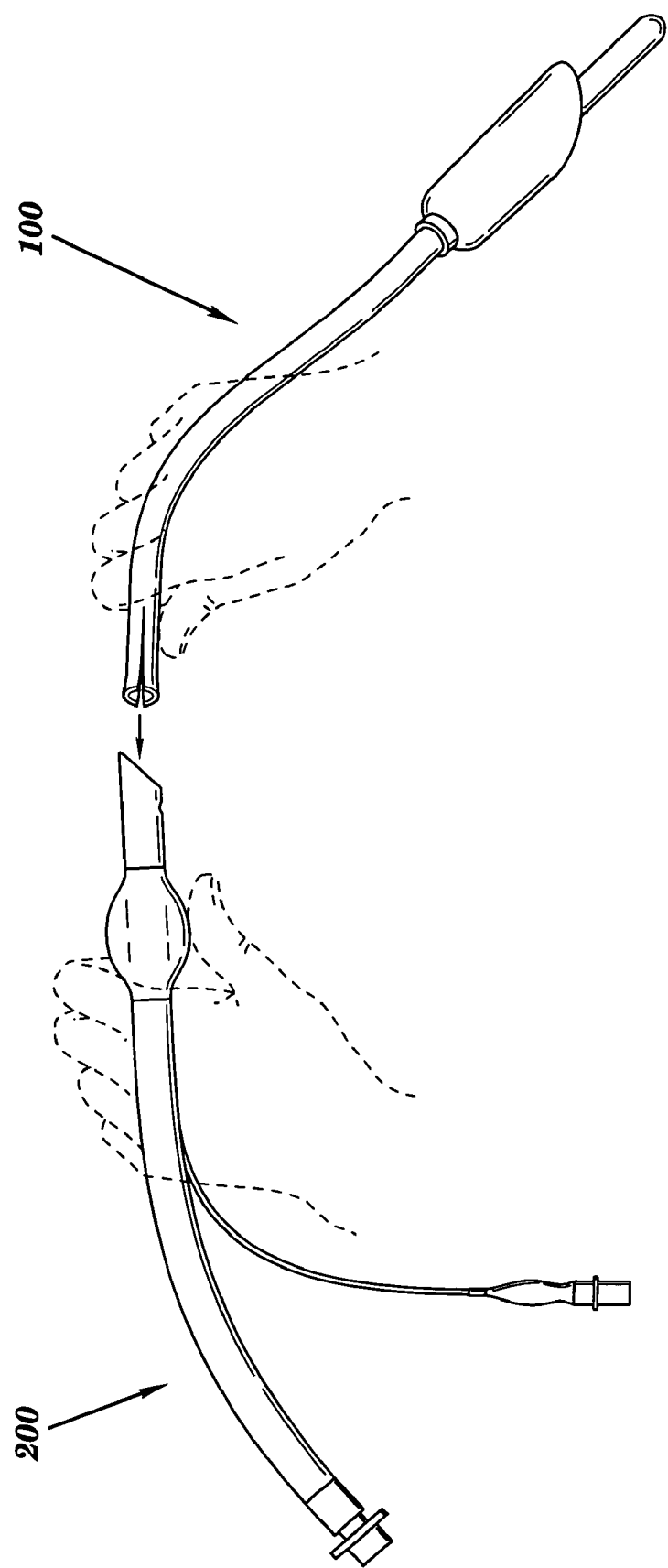
FIG. 1 is a schematic illustration of a flexible endotracheal tube introducer oriented for slidably removable disposition within an exemplary endotracheal tube.

As show in FIG. 1, the present invention comprises a flexible endotracheal tube introducer ("introducer") 100 for slidably removable disposition within an exemplary endotracheal tube ("ETT") 200, such as, for example, a No. 6.5, No. 7.0, No. 7.5 or No. 8.0 adult ETT.

Figure 2:
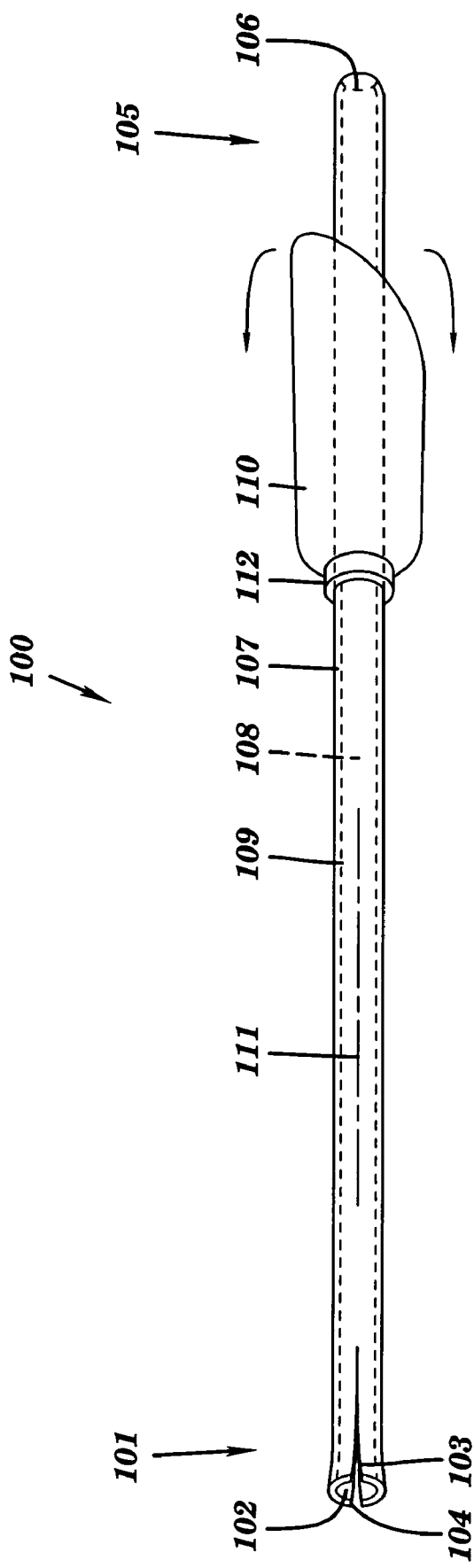
FIG. 2 is a schematic illustration of a flexible endotracheal tube introducer.

As shown in FIG. 2, introducer 100 comprises a tubular member 109 having a longitudinal axis 111, and having a lumen 108, extending between a split proximal end 101 and a distal end 105 of tubular member 109 and defined by a cylindrical wall 107 that is circumscribed by a ring 112 to which there is invertibly attached a shroud 110.

Cylindrical wall 107 of introducer 100 has an inner diameter of about 4.5 millimeters, a thickness of about 1 millimeter and an outer diameter of about 6.5 millimeters. Cylindrical wall 107 of introducer 100 has an outer diameter that is less than an inner diameter of exemplary ETT 200 (shown in FIG. 1).

A first slit 103 in split proximal end 101 of tubular member 109 extends distal-ward for about 1.5 centimeters from a proximal opening 102 of tubular member 109. A second slit 104 in split proximal end 101 of tubular member 109 is generally parallel to first slit 103 and extends distal-ward for about 1.5 centimeters from proximal opening 102 of tubular member 109, beginning at a point on cylindrical wall 107 that is about 180 degrees away from first slit 103.

Ring 112 is adherently fixed to tubular member 109 at a distance of about 4 centimeters from distal end 105 of tubular member 109. Ring 112 has a radial thickness of about 1 mm and a length of about 1 cm.

Figure 3A:
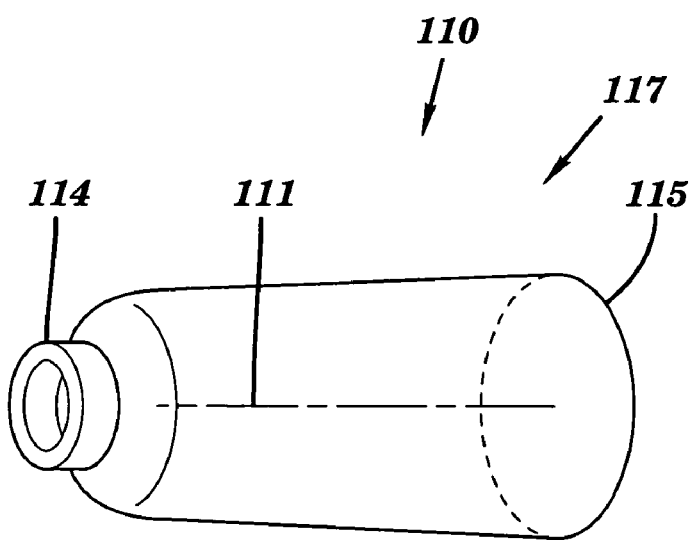
FIG. 3A is a schematic illustration of a shroud of a flexible endotracheal tube introducer in a first substantially frusto-conical shape.

FIG. 3A shows that shroud 110 may have a first substantially frusto-conical shape 117 that extends from a first circle 114 in a first plane that is perpendicular to longitudinal axis 111 of tubular member 109 (FIG. 1) and a second circle 115 in a second plane that is parallel to the first plane of first circle 114. Second circle 115 of shroud 110 is generally coaxial with tubular member 109 (FIG. 1) and is unattached to tubular member 109 (FIG. 1).

Figure 3B:
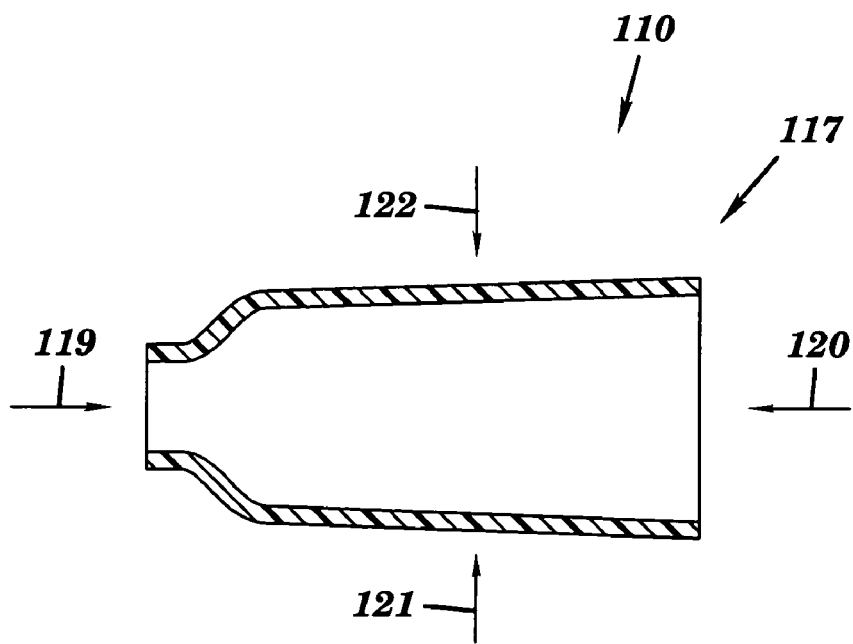
FIG. 3B is a schematic illustration showing a longitudinal (sagittal) cross section of a first substantially frusto-conical shape of a shroud of a flexible endotracheal tube introducer.

FIG. 3b shows a longitudinal cross sectional view taken through first substantially frusto-conical shape 117 of shroud 110, appearing generally as a parallelepiped having proximal side 119, distal side 120, anterior side 121 and posterior side 122.

In FIG. 3b, proximal side 119 measures about 6.5 millimeters, distal side 120 measures about 12 millimeters, anterior side 121 measures about 26 millimeters and posterior side 122 measures about 26 millimeters.

Figure 4A:
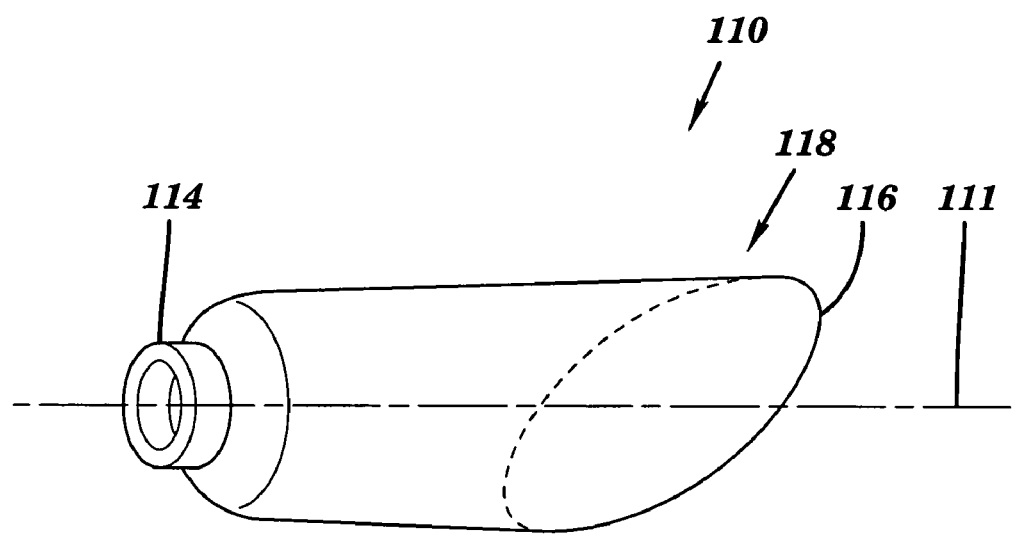
FIG. 4A is a schematic illustration of a shroud of a flexible endotracheal tube introducer in a second substantially frusto-conical shape.

FIG. 4A shows that shroud 110 may also have a second substantially frusto-conical shape 118 that extends from first circle 114 in a first plane that is perpendicular to longitudinal axis 111 of tubular member 109 (FIG. 1) to an ellipse 116 in a second plane that is either parallel or other than parallel to the first plane of first circle 114. Ellipse 116 is unattached to tubular member 109 (FIG. 1).

Figure 4B:
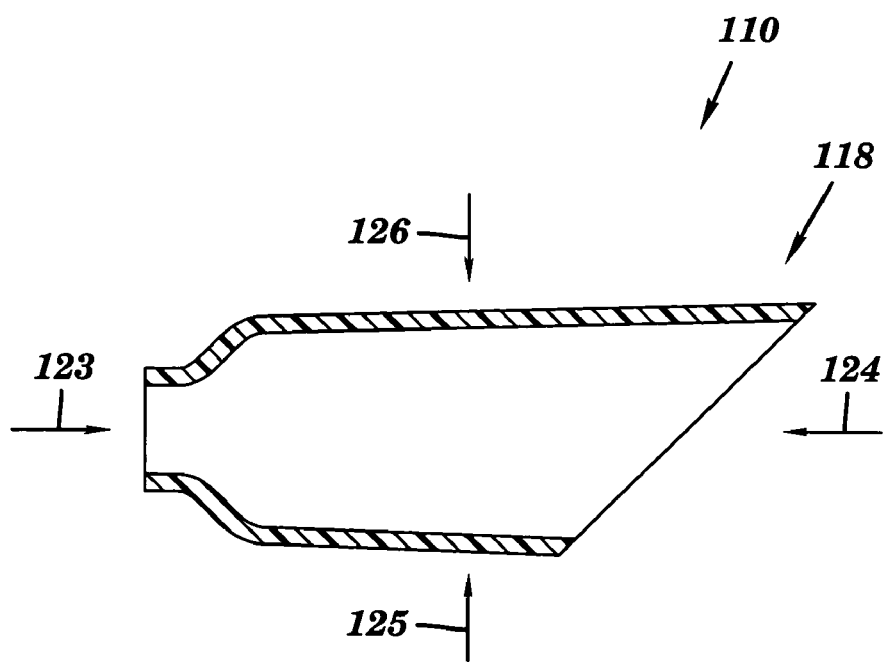
FIG. 4B is a schematic illustration showing a longitudinal (sagittal) cross section of a second substantially frusto-conical shape of a shroud of a flexible endotracheal tube introducer.

FIG. 4B shows a longitudinal cross-sectional view taken through second substantially frusto-conical shape 118 of shroud 110, appearing generally as a parallelepiped having proximal side 123, distal side 124, anterior side 125 and posterior side 126.

In FIG. 4B, proximal side 123 measures about 6.5 millimeters, distal side 124 measures about 13 millimeters, anterior side 125 measures about 26 millimeters and posterior side 126 measures about 33 millimeters.

Ring 112 (FIG. 2) may be manufactured, for example, from silicone, nylon or plastic, as a discrete structure to which shroud 110 is invertibly attached at first circle 114, or it may be fashioned as an extruded cylinder that is a proximal-ward extension ("neck") of shroud 110 at first circle 114. Alternatively, ring 112 may be formed as a ring-like radial extrusion of tubular member 109.

With ring 112 serving as a circumferential pivot about tubular member 109, shroud 110 may be inverted about ring 112 to assume two conformations: [i] an anteflexed, forward or distal-ward conformation; and, a [ii] a retroflexed, rearward or proximal-ward conformation.

Figure 5A:
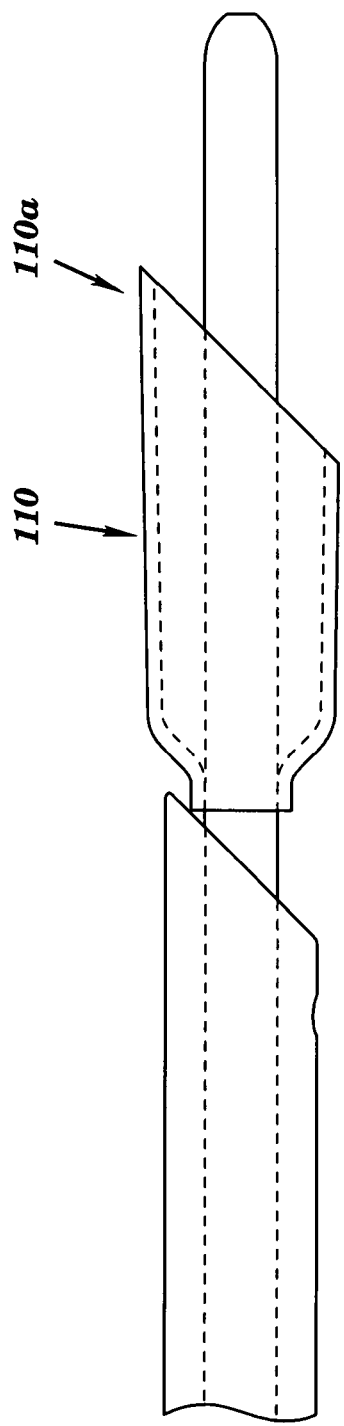
FIG. 5A shows a shroud of a flexible endotracheal tube introducer in an anteflexed, forward, or distal-ward conformation.
Figure 5B:
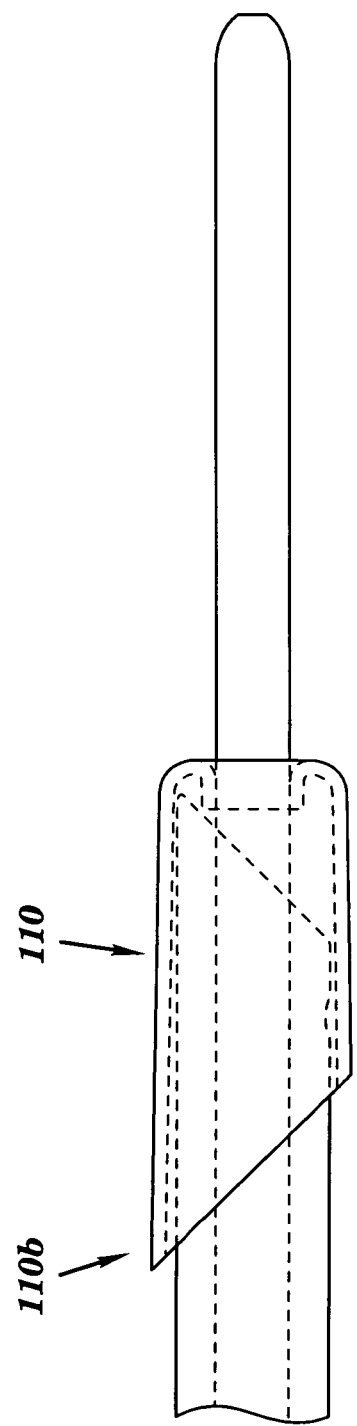
FIG. 5B shows a shroud of a flexible endotracheal tube introducer in a retroflexed, rearward, or proximal-ward conformation

FIG. 5A shows shroud 110 in the anteflexed, forward or distal-ward conformation 110a. FIG. 5B shows shroud 110 in the retroflexed, rearward or proximal-ward conformation 110b.

Figure 6:
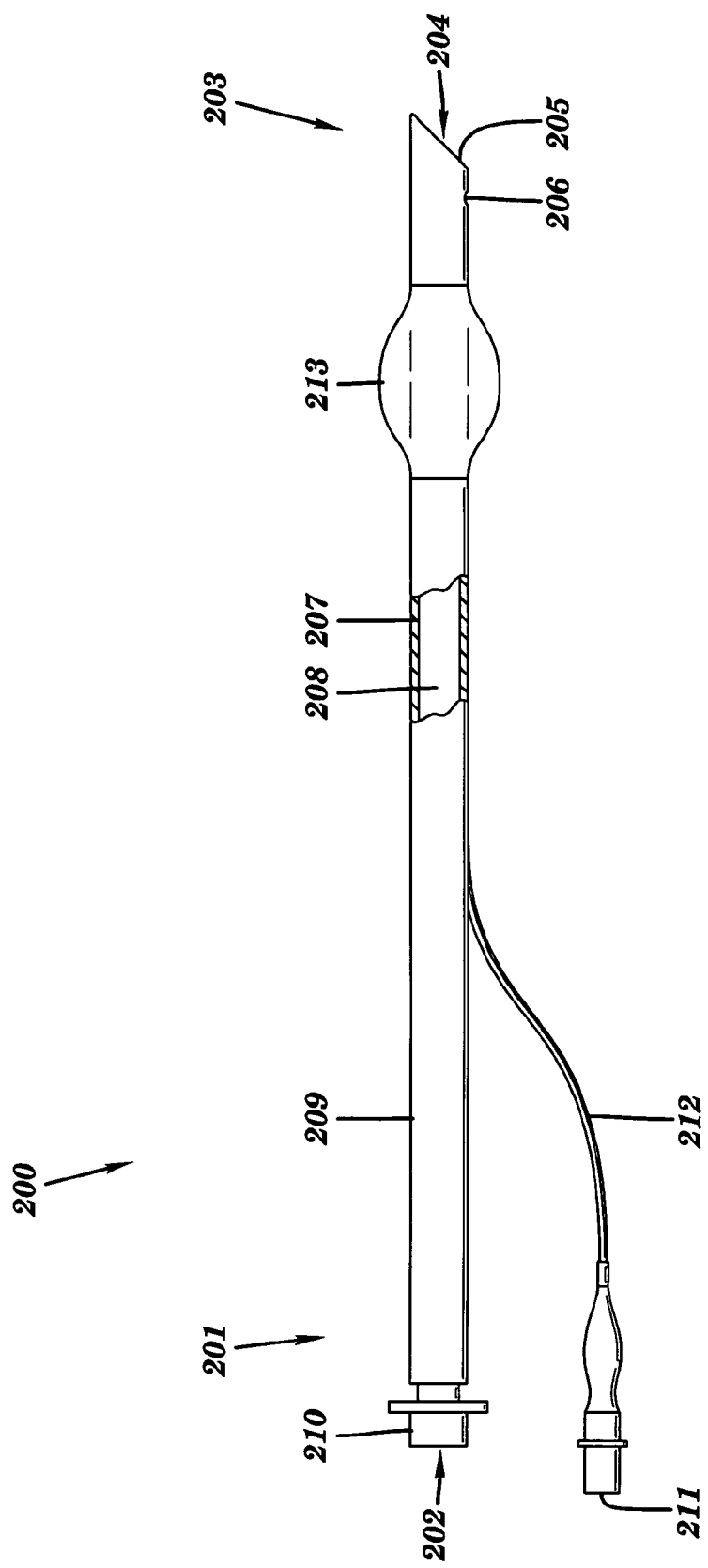
FIG. 6 is a schematic illustration of an exemplary endotracheal tube.

FIG. 6 shows an exemplary ETT 200 in greater detail, comprising an ETT tubular member 209 having an ETT lumen 208 for gas flow, defined by a cylindrical ETT wall 207, extending between a proximal opening 202 at a proximal ETT end 201 and a distal opening 204 at a distal ETT end 203 of ETT tubular member 209. Cylindrical wall 207 of ETT 200 has an inner diameter that is greater than the outer diameter of introducer 100 (FIG. 2).

Inflatable cuff or balloon 213 circumscribes ETT tubular member 209 adjacent distal ETT end 203 and communicates with an inflation port 211 via inflation tubing 212. Proximal end 201 of tubular member 209 is adapted to receive a connector piece 210 into which tubing (not shown in FIG. 6) for gas flow to a patient may be attached.

Distal ETT end 203 of ETT tubular member 209 terminates in a beveled tip whose shorter terminus 205 defines the anterior aspect of ETT 200. A Murphy eye 206 is fashioned into cylindrical wall 207 of ETT tubular member 209 adjacent distal end 203 to provide an alternative pathways for gas flow to a patient should distal opening 204 of ETT tubular member 209 become occluded.

Figure 7A:
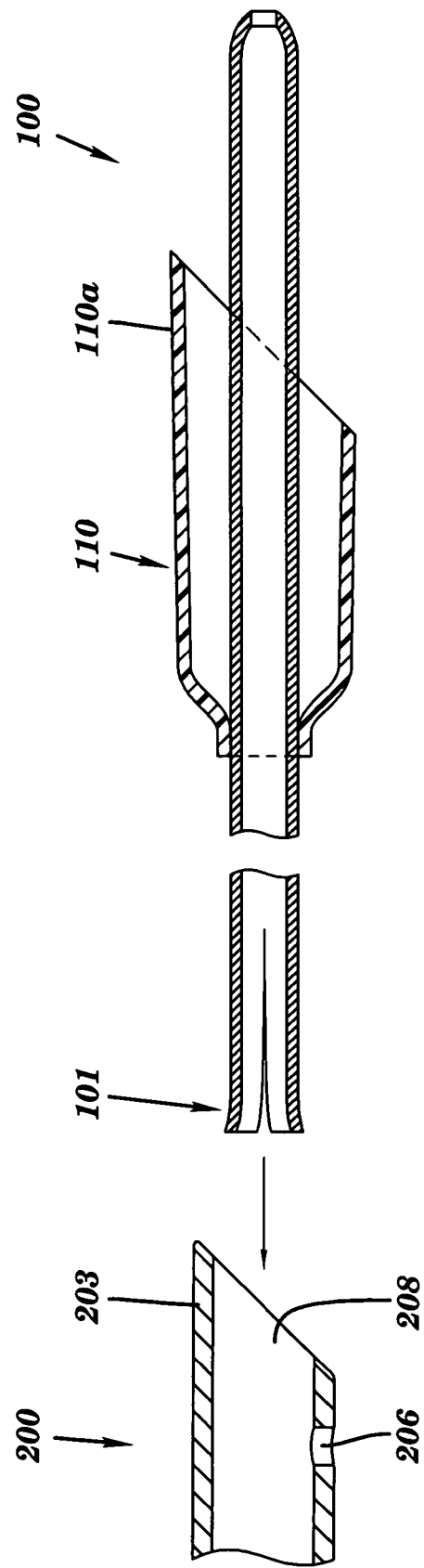
FIG. 7A is a schematic illustration showing a flexible endotracheal tube introducer with its shroud in its anteflexed, forward or distal-ward conformation and having its proximal end placed within a lumen at a distal end of an endotracheal tube.

In an orotracheal intubation, introducer 100 is grasped with shroud 110 in its anteflexed, forward or distal-ward position 110a, as shown in FIG. 7A. Split proximal end 101 of introducer 100 is placed within ETT lumen 208 at distal end 203 of ETT 200 (FIG. 7A) and advanced into ETT 200 until a proximal end of said invertibly attached shroud, such as ring 112 of introducer 100, apposes beveled distal tip 205 of ETT 200, as shown in FIG. 7B. Shroud 110 is then manually flexed from its anteflexed, forward or distal-ward position 110a to its retroflexed, rearward or proximal-ward position 110b to cover beveled tip 205 and Murphy eye 206 of ETT 200, as shown in FIG. 7C.

Figures 1, 7D:
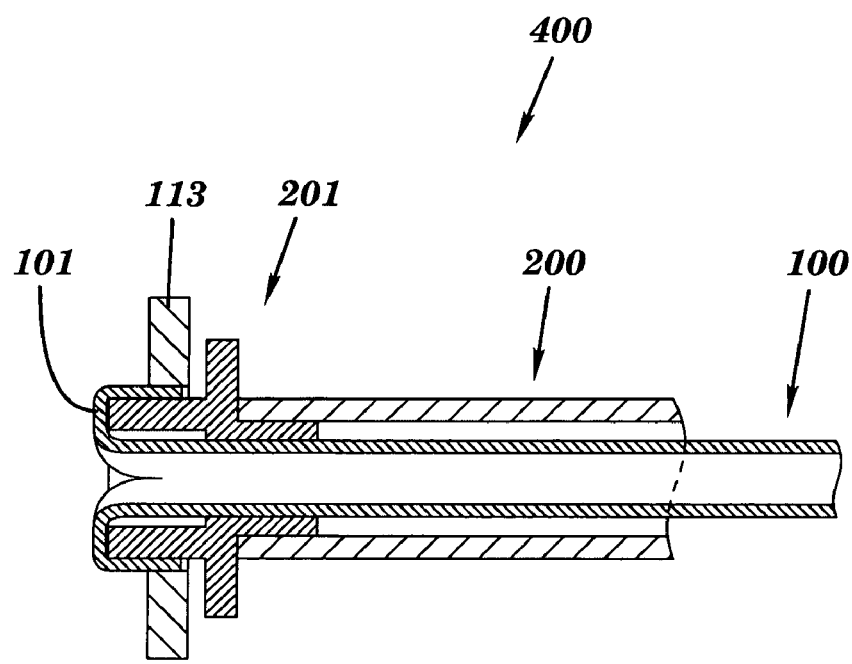
Figures 2, 7D:
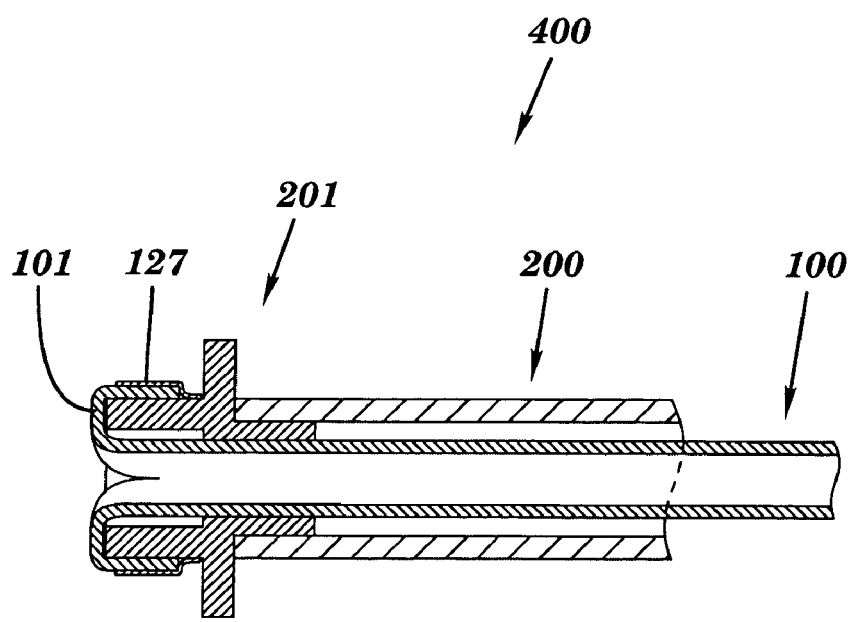

Split proximal end 101 of introducer 100 is then fixed to proximal end 201 of ETT 200 by everting the split halves of proximal end 101 of introducer 100 over proximal end 201 of ETT 200, as shown in FIGS. 7D-1 and 7D-2, using, for example, surgical tape [127] as shown in FIG. 7D-2 or a fixation ring 113 as shown in FIG. 7D-2, to stabilize the alignment of the respectively shrouded distal ends 105 and 203 of introducer 100 and ETT 200, now combined as introducer-ETT unit 400, the proximal aspect of which is shown in FIGS. 7D-1 and 7D-2.

Lubrication must be generously applied between shroud 110 of introducer 100 and distal end 203 of ETT 200 to prevent sticking during subsequent withdrawal of introducer 100 from lumen 208 of ETT 200.

Figure 7E:
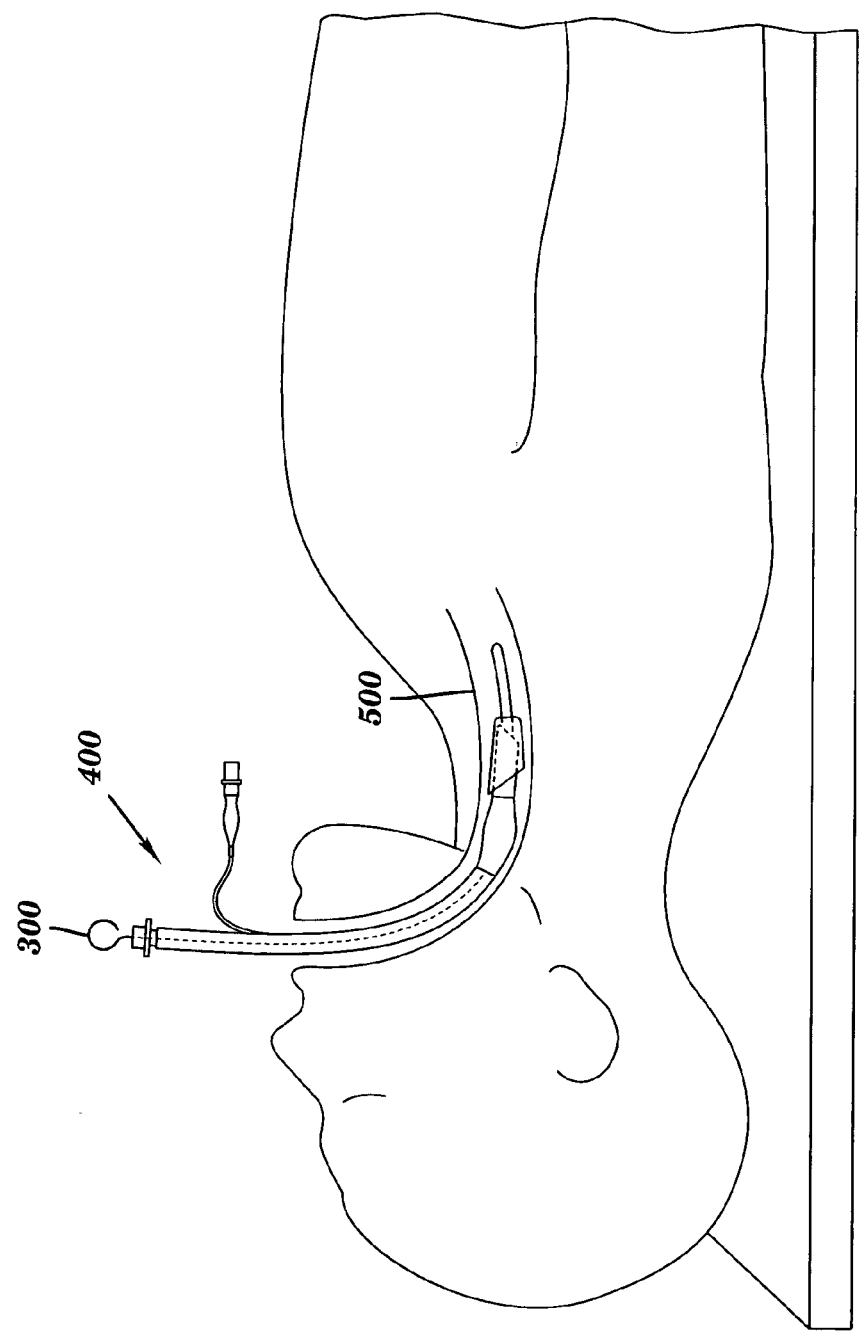
FIG. 7E is a schematic illustration showing a combined endotracheal tube introducer-endotracheal tube unit with a malleable stylet in place in a patient's airway.
Figure 7H:
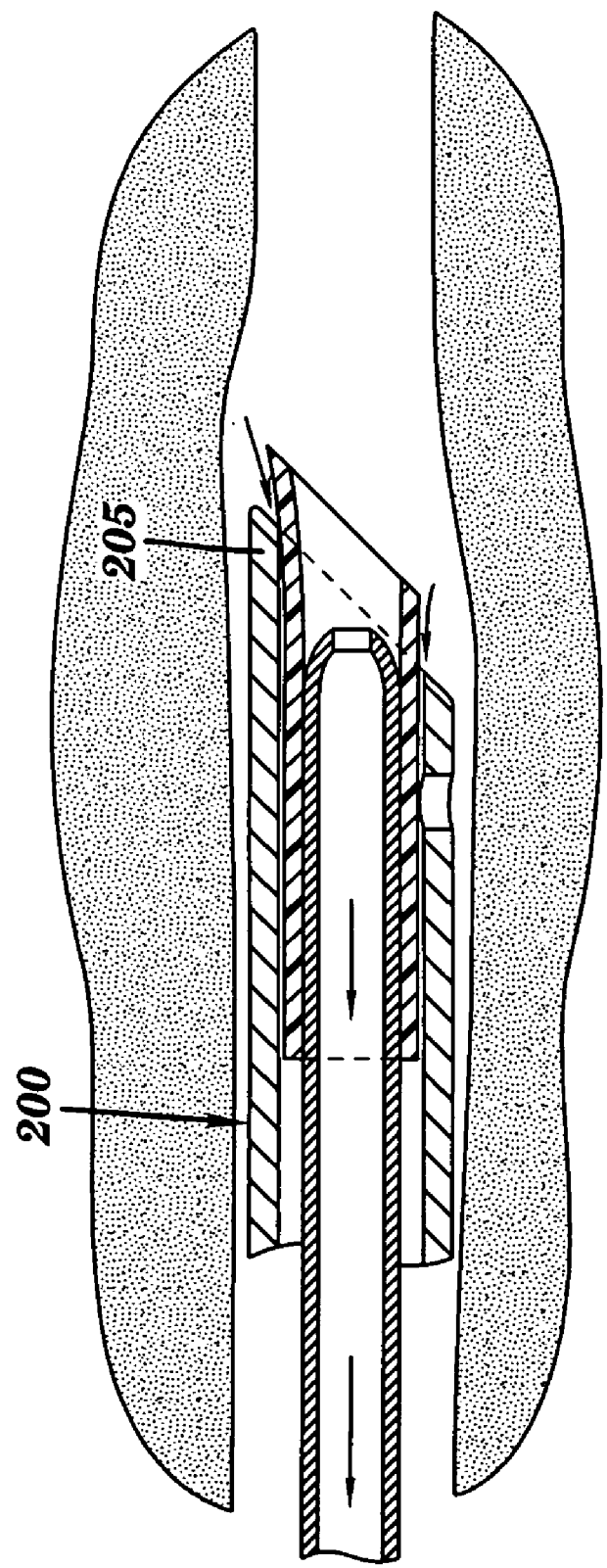
FIG. 7H is a schematic illustration showing a shroud of a flexible endotracheal tube introducer in its anteflexed, forward or distal-ward conformation as it is being withdrawn from an endotracheal tube.

A malleable stylet 300, shown in FIG. 7E, is inserted into lumen 108 of introducer 100, now forming combined introducer-ETT unit 400. Combined introducer-ETT unit 400 is advanced into a patient's airway 500, as shown in FIG. 7E, to place the shrouded end of combined introducer-ETT unit 400 between and beyond the patient's vocal cords (not shown in FIG. 7E).

Surgical tape 127 or fixation ring 113 is now removed and introducer 100 is withdrawn from ETT 200. During the withdrawal of introducer 100 from ETT 200, shroud 110 is anteflexed to forward, distal-ward conformation 110a by the sliding motion of distal end 203 of ETT 200 relative to wall 107 of introducer 100, as shown in sequential FIGS. 7F through 7G, when viewed from left to right.

In a nasal intubation, introducer 100 is grasped with shroud 110 in its anteflexed, forward or distal-ward position 110a, as shown in FIG. 7A. Split proximal end 101 of introducer 100 is placed within ETT lumen 208 at distal end 203 of ETT 200 (FIG. 7A) and advanced into ETT 200 until a proximal end of invertibly attached shroud 110, such as ring 112 of introducer 100, apposes beveled distal tip 205 of ETT 200, as shown in FIG. 7B. Shroud 110 is then manually flexed from its anteflexed, forward or distal-ward position 110a to its retroflexed, rearward or proximal-ward position 110b to cover beveled tip 205 and Murphy eye 206 of ETT 200, as shown in FIG. 7C.

Split proximal end 101 of introducer 100 is then fixed to proximal end 201 of ETT 200 by everting the split halves of proximal end 101 of introducer 100 over proximal end 201 of ETT 200, as shown in FIGS. 7D-1 and 7D-2, using, for example, surgical tape 127 as shown in FIG. 7D-2 or a fixation ring 113 as shown in FIG. 7D-2, to stabilize the alignment of the respectively shrouded distal ends 105 and 203 of introducer 100 and ETT 200, now combined as introducer-ETT unit 400, the proximal aspect of which is shown in FIGS. 7D-1 and 7D-2.

Lubrication must be generously applied between shroud 110 of introducer 100 and distal end 203 of ETT 200 to prevent sticking during subsequent withdrawal of introducer 100 from lumen 208 of ETT 200.

Combined introducer-ETT unit 400 is advanced into a patient's nostril and thence into the patient's nasopharynx until combined introducer-ETT unit 400 is visualized through the patient's mouth in the patient's oropharynx. Thereafter, the shrouded distal end of combined introducer-ETT unit 400 is grasped with a forceps introduced through the patient's mouth and thence directed so as to place the shrouded distal end of combined introducer-ETT unit 400 between and beyond the patient's vocal cords (not shown in FIG. 7E).

Surgical tape 127 or fixation ring 113 is now removed and introducer 100 is withdrawn from ETT 200. During the withdrawal of introducer 100 from ETT 200, shroud 110 is anteflexed to forward, distal-ward conformation 110 by the sliding motion of distal end 203 of ETT 200 relative to wall 107 of introducer 100, as shown in sequential FIGS. 7F through 7G, when viewed from left to right.

In an intubation using a fiberscope, introducer 100 is grasped with shroud 110 in its anteflexed, forward or distal-ward position 110a, as shown in FIG. 7A. Split proximal end 101 of introducer 100 is placed within ETT lumen 208 at distal end 203 of ETT 200 (FIG. 7A) and advanced into ETT 200 until a proximal end of invertibly attached shroud 110, such as ring 112 of introducer 100, apposes beveled distal tip 205 of ETT 200, as shown in FIG. 7B. Shroud 110 is then manually flexed from its anteflexed, forward or distal-ward position 110a to its retroflexed, rearward or proximal-ward position 110b to cover beveled tip 205 and Murphy eye 206 of ETT 200, as shown in FIG. 7C.

Split proximal end 101 of introducer 100 is then fixed to proximal end 201 of ETT 200 by everting the split halves of proximal end 101 of introducer 100 over proximal end 201 of ETT 200, as shown in FIGS. 7D-1 and 7D-2, using, for example, surgical tape 127 as shown in FIG. 7D-2 or a fixation ring 113 as shown in FIG. 7D-2, to stabilize the alignment of the respectively shrouded distal ends 105 and 203 of introducer 100 and ETT 200, now combined as introducer-ETT unit 400, the proximal aspect of which is shown in FIGS. 7D-1 and 7D-2.

Lubrication must be generously applied between shroud 110 of introducer 100 and distal end 203 of ETT 200 to prevent sticking during subsequent withdrawal of introducer 100 from lumen 208 of ETT 200.

Figure 8A:
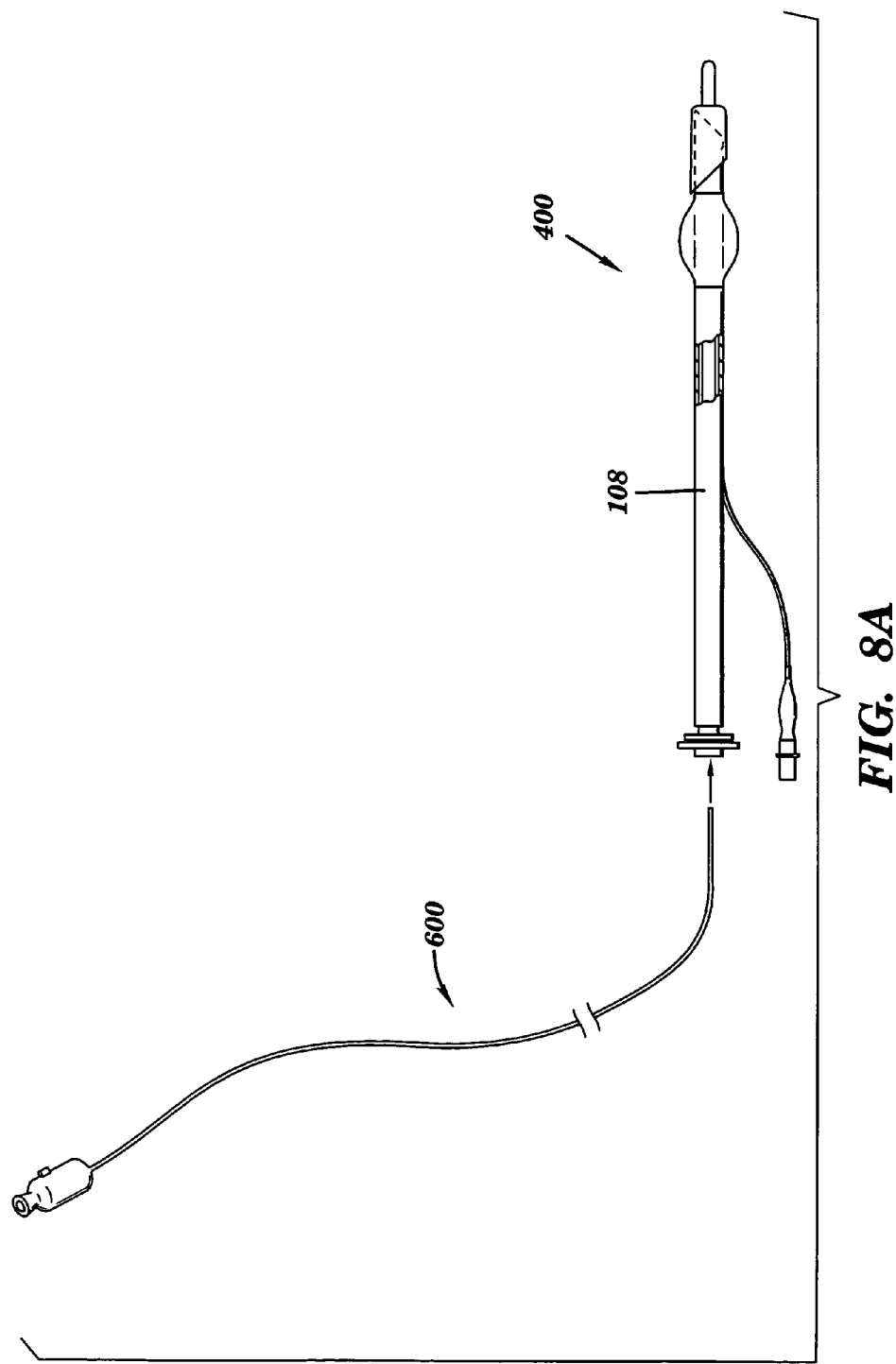
FIG. 8A is a schematic illustration of a combined introducer-ETT unit about to be advanced over a fiberscope.
Figure 8B:
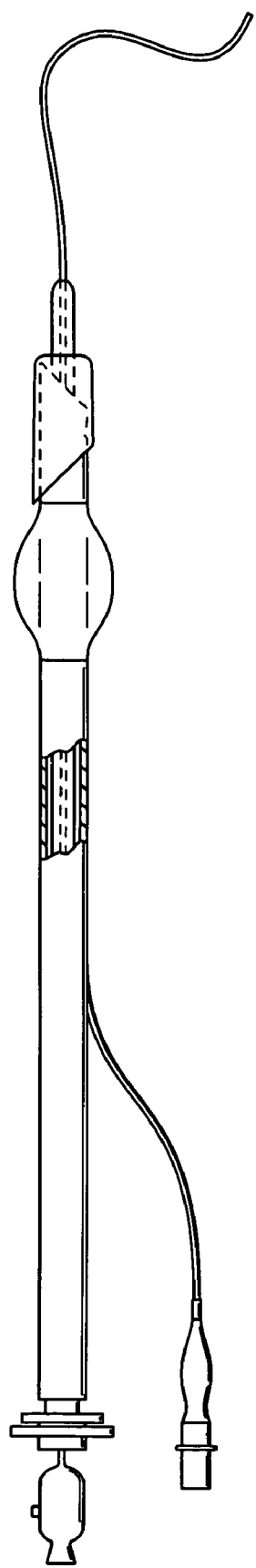
FIG. 8B is a schematic illustration of a combined introducer-ETT unit piggy backed upon a fiberscope.
Figure 8C:
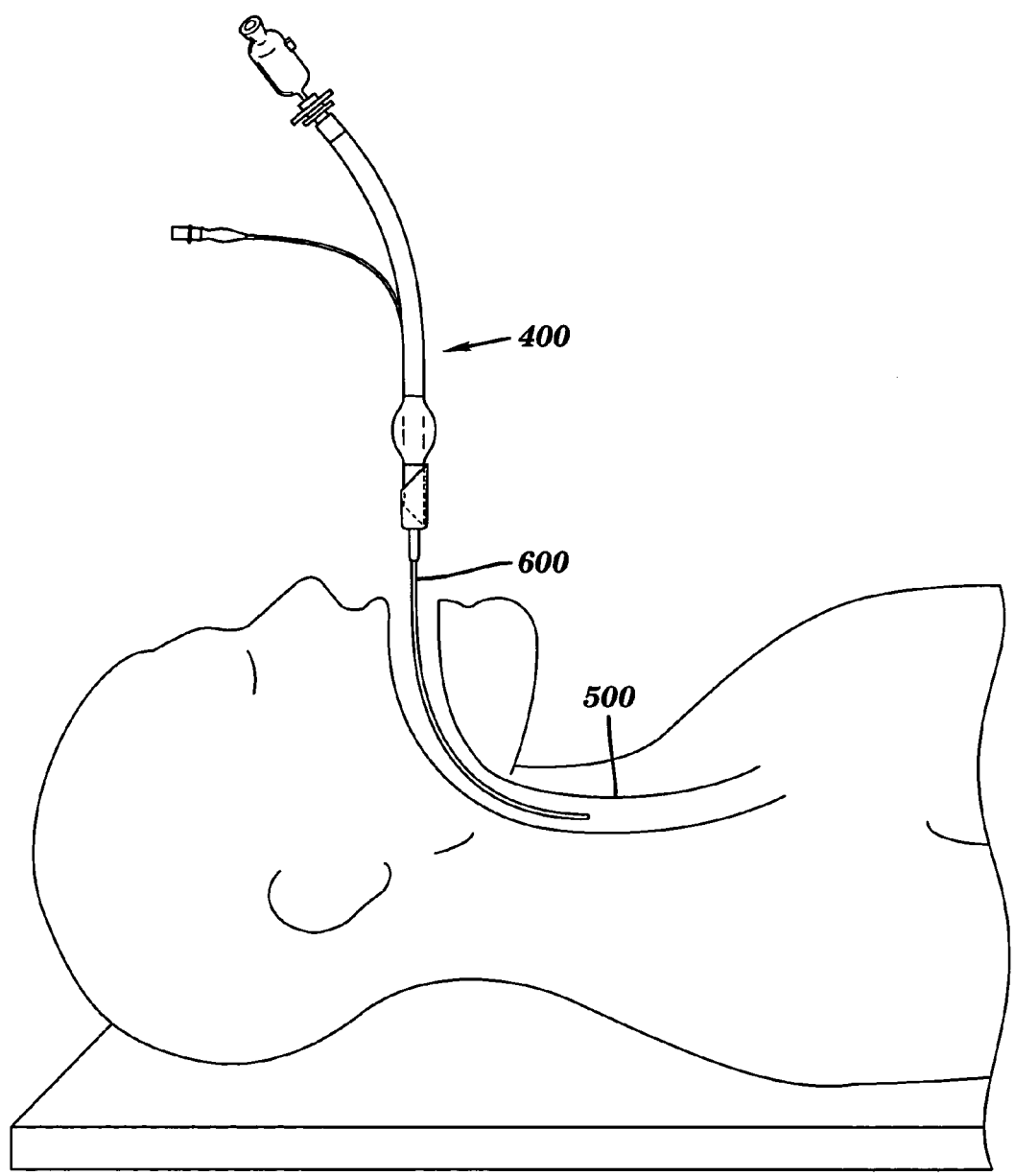
FIG. 8C is a schematic illustration of a combined introducer-ETT unit piggy backed upon a fiberscope and about to be advanced into a patient's airway.

As shown in FIG. 8A, a fiberscope 600 is then inserted within lumen 108 of introducer 100, now forming combined introducer-ETT unit 400. With introducer-ETT unit 400 effectively "piggy-backed" upon fiberscope 600, as shown in FIG. 8B, fiberscope 600 is introduced into a patient's airway and is used to identify the patient's carina. Having identified the patient's carina, combined introducer-ETT unit 400 is advanced over fiberscope 600, using fiberscope 600 as a guide wire, (FIG. 8C) so as to place the shrouded distal end of combined introducer-ETT unit 400 between and beyond the patient's vocal cords (not shown in FIG. 8C).

Surgical tape 127 or fixation ring 113 is now removed and introducer 100 is withdrawn from ETT 200. During the withdrawal of introducer 100 from ETT 200, shroud 110 is anteflexed to forward, distal-ward conformation 110a by the sliding motion of distal end 203 of ETT 200 relative to wall 107 of introducer 100, as shown in sequential FIGS. 7F through 7G, when viewed from left to right.

In an endotracheal tube exchange, introducer 100 is grasped with shroud 110 in its anteflexed, forward or distal-ward position 110a, as shown in FIG. 7A. Split proximal end 101 of introducer 100 is placed within ETT lumen 208 at distal end 203 of ETT 200 (FIG. 7A) and advanced into ETT 200 until a proximal end of invertibly attached shroud 110, such as ring 112 of introducer 100, apposes beveled distal tip 205 of ETT 200, as shown in FIG. 7B. Shroud 110 is then manually flexed from its anteflexed, forward or distal-ward position 110a to its retroflexed, rearward or proximal-ward position 110b to cover beveled tip 205 and Murphy eye 206 of ETT 200, as shown in FIG. 7C.

Split proximal end 101 of introducer 100 is then fixed to proximal end 201 of ETT 200 by everting the split halves of proximal end 101 of introducer 100 over proximal end 201 of ETT 200, as shown in FIGS. 7D-1 and 7D-2, using, for example, surgical tape 127 as shown in FIG. 7D-2 or a fixation ring 113 as shown in FIG. 7D-2, to stabilize the alignment of the respectively shrouded distal ends 105 and 203 of introducer 100 and ETT 200, now combined as introducer-ETT unit 400, the proximal aspect of which is shown in FIGS. 7D-1 and 7D-2.

Lubrication must be generously applied between shroud 110 of introducer 100 and distal end 203 of ETT 200 to prevent sticking during subsequent withdrawal of introducer 100 from lumen 208 of ETT 200.

Figure 9A:
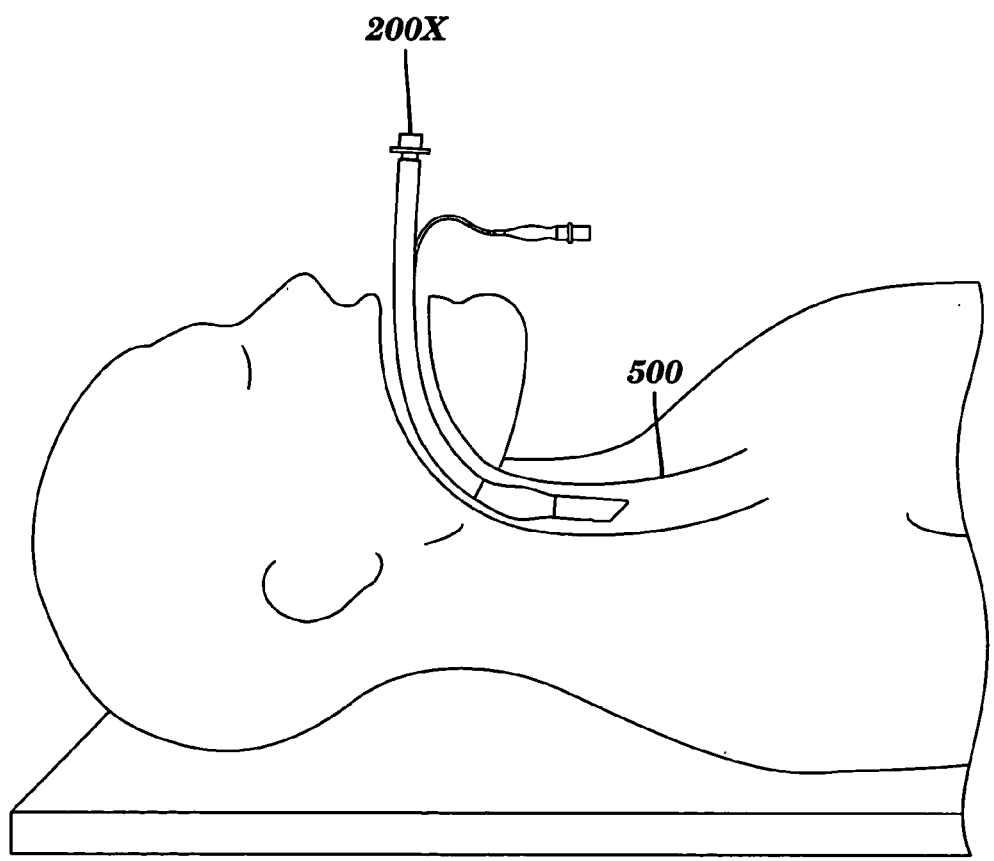
FIG. 9A is a schematic illustration of an in-place ETT in a patient's airway.
Figure 9B:
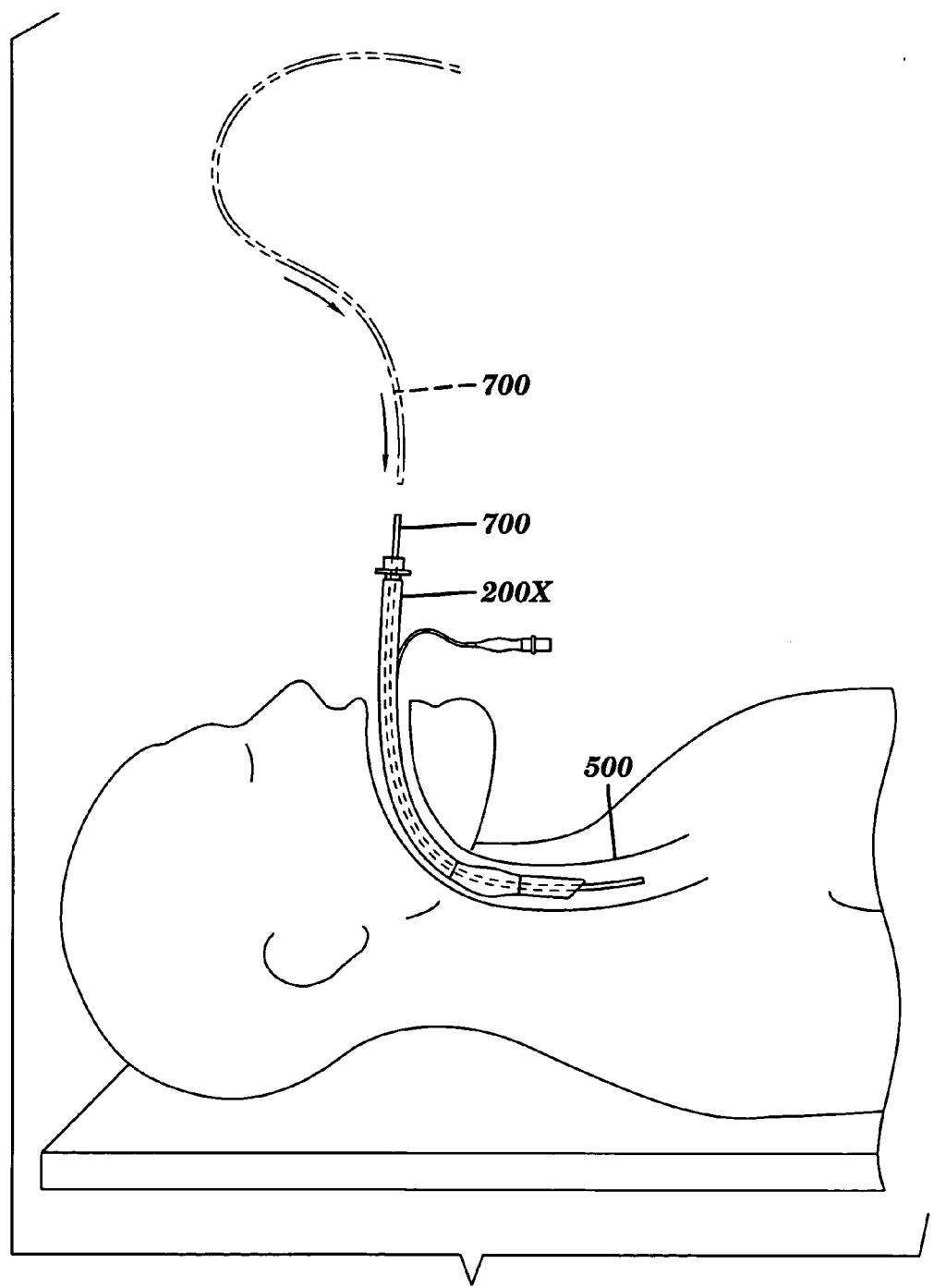
FIG. 9B is a schematic illustration of an in-place ETT in a patient's airway, into which in-place ETT a tube exchanger has been inserted.
Figure 9C:
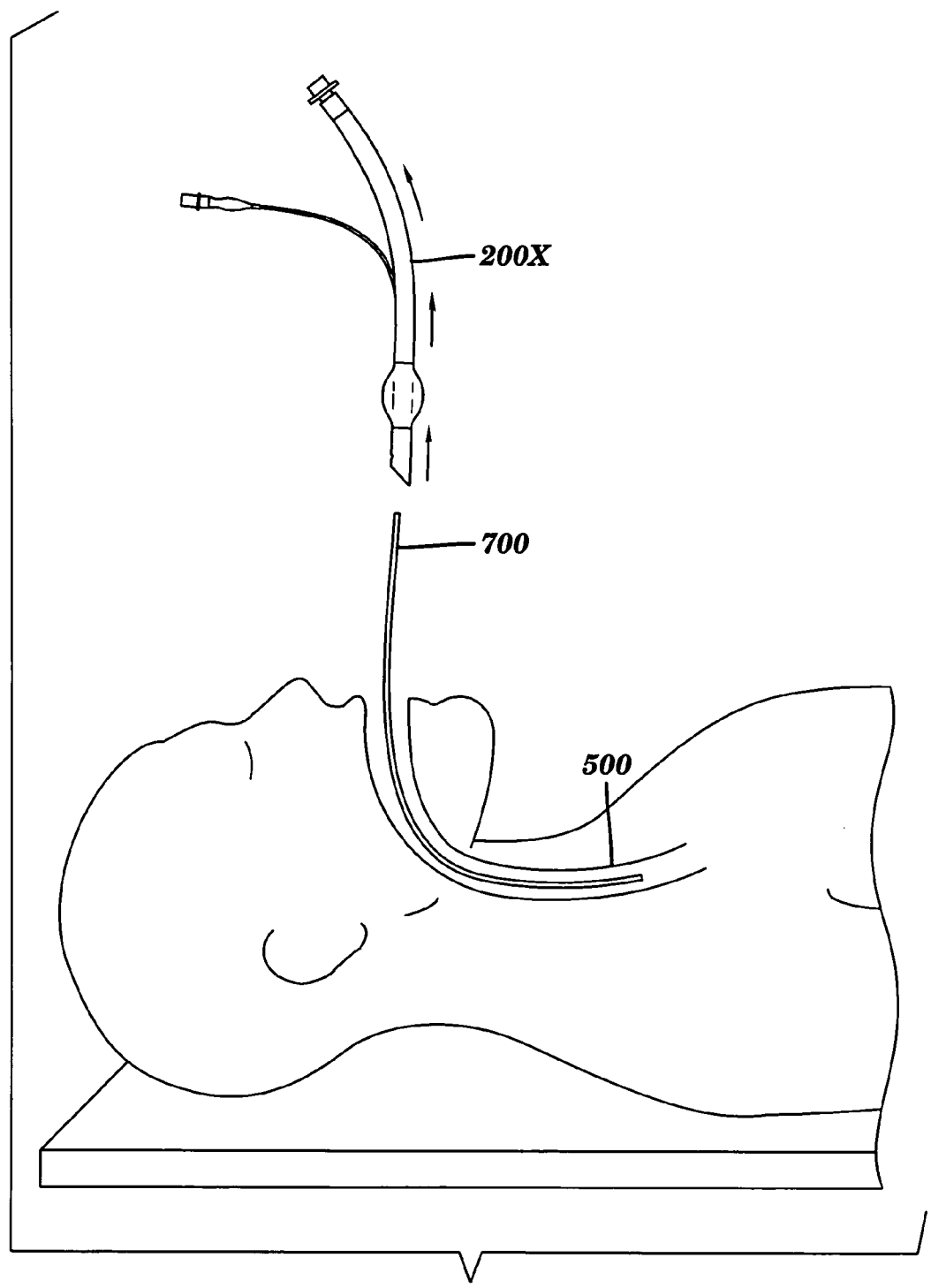
FIG. 9C is a schematic illustration of in-place ETT having been withdrawn over a tube exchanger and removed from a patient's airway.
Figure 9D:
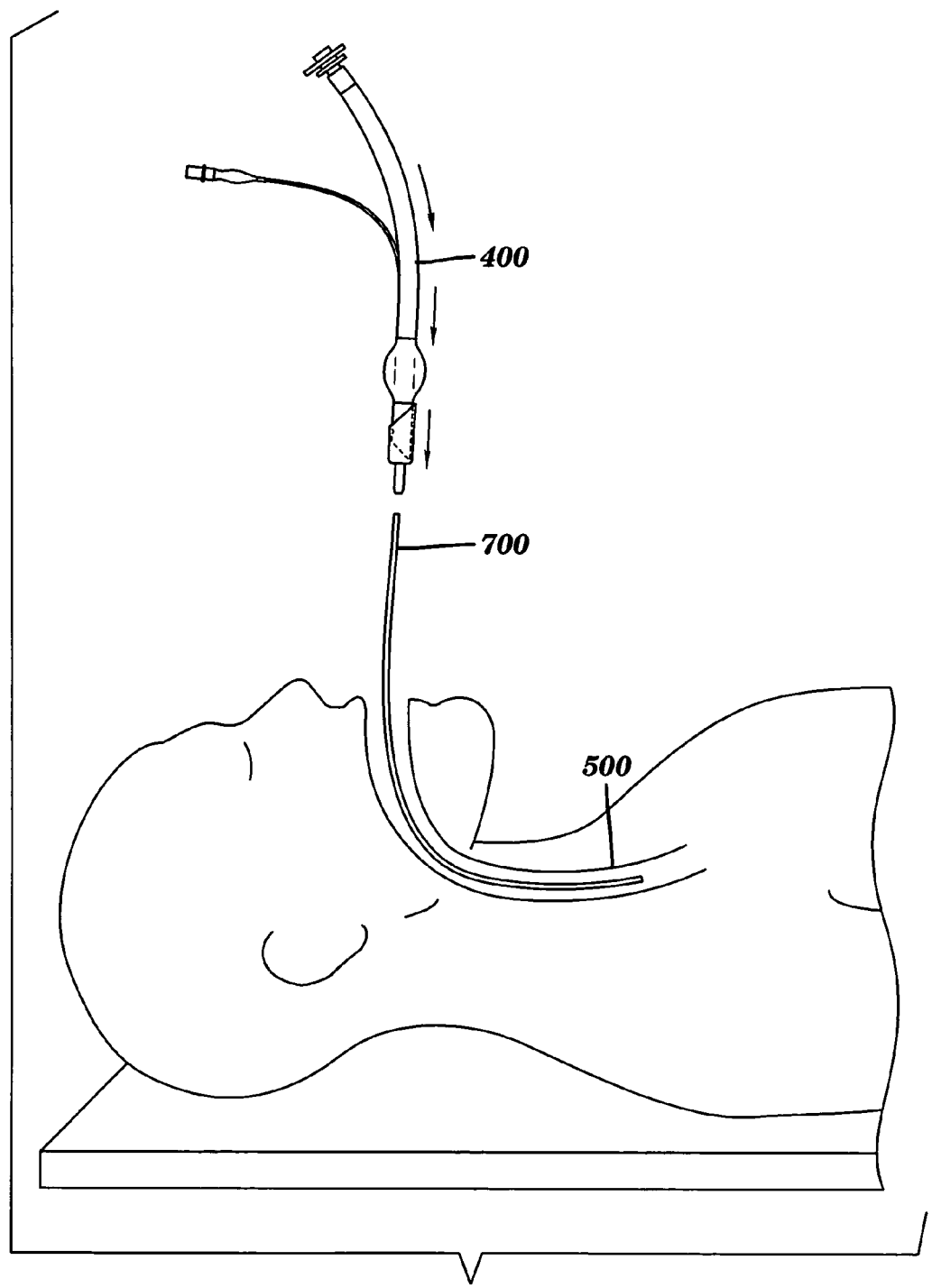
FIG. 9D is a schematic illustration of a combined introducer-ETT unit about to be advanced over a tube exchanger into a patient's airway.

By analogy with the use of fiberscope 600, a tube exchanger 700 is now inserted into an in-place ETT 200x within a patient's airway 500 to serve as a guide wire for removal of in-place ETT 200x (FIG. 9A and FIG. 9B). In-place ETT 200x is withdrawn over tube exchanger 700 (FIG. 9C) and thereafter combined introducer-ETT unit 400 is advanced over tube exchanger 700, using tube exchanger 700 as a guide wire (FIG. 9D), so as to place the shrouded distal end of combined introducer-ETT unit 400 between and beyond the patient's vocal cords (not shown in FIGS. 9A–9D).

Surgical tape 127 or fixation ring 113 is now removed and introducer 100 is withdrawn from ETT 200. During the withdrawal of introducer 100 from ETT 200, shroud 110 is anteflexed to forward, distal-ward conformation 110a by the sliding motion of distal end 203 of ETT 200 relative to wall 107 of introducer 100, as shown in sequential FIGS. 7F through 7G, when viewed from left to right, leaving said ETT 200 properly positioned in the patient's trachea.

What is claimed is:

1. An endotracheal tube introducer ("introducer") for slidably removable disposition within an endotracheal tube ("ETT"), said introducer comprising a tube having a wall defining a lumen extending between a split proximal end and a distal end of said introducer; said wall having an outer diameter that is less than an inner diameter of said ETT and having a shroud invertibly attached to a ring circumscribing said introducer; said ring forming a circumferential pivot for distal-ward ("forward") flexion and proximal-ward ("rearward") flexion of said shroud with respect to said ring; and, wherein said shroud has a substantially frusto-conical shape extending from a circle in a first plane that is coincident with said ring and perpendicular to a longitudinal axis of said introducer, to a closed conic section in a second plane, said closed conic section being generally coaxial with and unattached to said introducer.

2. A method for performing an intubation using an endotracheal tube ("ETT") and an endotracheal tube introducer ("introducer"), said introducer comprising a tube having a wall defining a lumen extending between a split proximal end and a distal end of said introducer; said wall having an outer diameter that is less than an inner diameter of said ETT and having a shroud invertibly attached to a ring circumscribing said introducer; said ring forming a circumferential pivot for forward flexion and rearward flexion of said shroud with respect to said ring; and, wherein said shroud has a substantially frusto-conical shape extending from a circle in a first plane that is coincident with said ring and perpendicular to a longitudinal axis of said introducer, to a closed conic section in a second plane, said closed conic section being generally coaxial with and unattached to said introducer, comprising the steps of:

a. placing said shroud of said introducer in a forward conformation;
b. placing said split proximal end of said introducer within a lumen of said ETT at a distal end thereof
c. advancing said split proximal end of said introducer into said lumen of said ETT until a proximal end of said shroud apposes a distal tip of said ETT;
d. manually flexing said shroud of said introducer from said forward conformation to a rearward conformation, thereby covering said distal tip of said ETT and a Murphy eye of said ETT;
e. fixing said split proximal end of said introducer to a proximal end of said ETT by means of surgical tape or a fixation ring, thereby stabilizing said distal end of said ETT and said distal end of said introducer and forming a combined introducer-ETT unit having a shrouded combined distal end;
f. lubricating a region between said shroud of said introducer and said distal end of said ETT with surgical lubricant to prevent sticking during subsequent withdrawal of said introducer from said lumen of said ETT;
d. introducing a malleable stylet within said lumen of said introducer forming said combined introducer-ETT unit;
e. advancing said shrouded combined introducer-ETT unit bearing said malleable stylet within said lumen of said introducer into a patient's airway;
f. directing said shrouded combined distal end of said combined introducer-ETT unit bearing said malleable stylet between and beyond a patient's vocal cords;
g. removing said surgical tape or said fixation ring and withdrawing said introducer from said ETT.

3. A method for performing an intubation using an endotracheal tube ("ETT") and an endotracheal tube introducer ("introducer"), said introducer comprising a tube having a wall defining a lumen extending between a split proximal end and a distal end of said introducer; said wall having an outer diameter that is less than an inner diameter of said ETT and having a shroud invertibly attached to a ring circumscribing said introducer; said ring forming a circumferential pivot for forward flexion and rearward flexion of said shroud with respect to said ring; and, wherein said shroud has a substantially frusto-conical shape extending from a circle in a first plane that is coincident with said ring and perpendicular to a longitudinal axis of said introducer, to a closed conic section in a second plane, said closed conic section being generally coaxial with and unattached to said introducer, comprising the steps of:

a. placing said shroud of said introducer in a forward conformation;
b. placing said split proximal end of said introducer within a lumen of said ETT at a distal end thereof;
c. advancing said split proximal end of said introducer into said lumen of said ETT until a proximal end of said shroud apposes a distal tip of said ETT;
d. manually flexing said shroud of said introducer from said forward conformation to a rearward conformation, thereby covering said distal tip of said ETT and a Murphy eye of said ETT;
e. fixing said split proximal end of said introducer to a proximal end of said ETT by means of surgical tape or a fixation ring, thereby stabilizing said distal end of said ETT and said distal end of said introducer and forming a combined introducer-ETT unit having a shrouded combined distal end;
f. lubricating a region between said shroud of said introducer and said distal end of said ETT with surgical lubricant to prevent sticking during subsequent withdrawal of said introducer from said lumen of said ETT;

g. advancing said combined introducer-ETT unit into a patient's nostril and thence into said patient's nasopharynx until said combined introducer-ETT unit is visualized through said patient's mouth in said patient's oropharynx;

h. grasping a shrouded distal end of said combined introducer-ETT unit with a forceps introduced through said patient's mouth and thence directing said shrouded distal end of said combined introducer-ETT unit so as to place said shrouded distal end of said combined introducer-ETT unit between and beyond said patient's vocal cords;

i. removing said surgical tape or said fixation ring and withdrawing said introducer from said ETT.

4. A method for performing an intubation using an endotracheal tube ("ETT") and an endotracheal tube introducer ("introducer"), said introducer comprising a tube having a wall defining a lumen extending between a split proximal end and a distal end of said introducer; said wall having an outer diameter that is less than an inner diameter of said ETT and having a shroud invertibly attached to a ring circumscribing said introducer; said ring forming a circumferential pivot for forward flexion and rearward flexion of said shroud with respect to said ring; and, wherein said shroud has a substantially frusto-conical shape extending from a circle in a first plane that is coincident with said ring and perpendicular to a longitudinal axis of said introducer, to a closed conic section in a second plane, said closed conic section being generally coaxial with and unattached to said introducer, comprising the steps of:

a. placing said shroud of said introducer in a forward conformation;

b. placing said split proximal end of said introducer within a lumen of said ETT at a distal end thereof;

c. advancing said split proximal end of said introducer into said lumen of said ETT until a proximal end of said shroud apposes a distal tip of said ETT;

d. manually flexing said shroud of said introducer from said forward conformation to a rearward conformation, thereby covering said distal tip of said ETT and a Murphy eye of said ETT;

e. fixing said split proximal end of said introducer to a proximal end of said ETT by means of surgical tape or a fixation ring, thereby stabilizing said distal end of said ETT and said distal end of said introducer and forming a combined introducer-ETT unit having a shrouded combined distal end;

f. lubricating a region between said shroud of said introducer and said distal end of said ETT with surgical lubricant to prevent sticking during subsequent withdrawal of said introducer from said lumen of said ETT;

g. inserting a fiberscope within said lumen of said introducer forming said combined introducer-ETT unit;

h. introducing said fiberscope into a patient's airway and using said fiberscope to identify said patent's carina;

i. advancing said combined introducer-ETT unit over said fiberscope into said patient's trachea using said fiberscope as a guide wire, so as to place said shrouded combined distal end of said combined introducer-ETT unit between and beyond said patient's vocal cords;

j. withdrawing said fiberscope from said combined introducer-ETT unit;

k. removing said surgical tape or said fixation ring and withdrawing said introducer from said ETT.

5. A method for performing an intubation using an endotracheal tube ("ETT") and an endotracheal tube introducer ("introducer"), said introducer comprising a tube having a wall defining a lumen extending between a split proximal end and a distal end of said introducer; said wall having an outer diameter that is less than an inner diameter of said ETT and having a shroud invertibly attached to a ring circumscribing said introducer; said ring forming a circumferential pivot for forward flexion and rearward flexion of said shroud with respect to said ring; and, wherein said shroud has a substantially frusto-conical shape extending from a circle in a first plane that is coincident with said ring and perpendicular to a longitudinal axis of said introducer, to a closed conic section in a second plane, said closed conic section being generally coaxial with and unattached to said introducer, comprising the steps of:

a. placing said shroud of said introducer in a forward conformation;

b. placing said split proximal end of said introducer within a lumen of said ETT at a distal end thereof;

c. advancing said split proximal end of said introducer into said lumen of said ETT until a proximal end of said shroud apposes a distal tip of said ETT;

d. manually flexing said shroud of said introducer from said forward conformation to a rearward conformation, thereby covering said distal tip of said ETT and a Murphy eye of said ETT;

e. fixing said split proximal end of said introducer to a proximal end of said ETT by means of surgical tape or a fixation ring, thereby stabilizing said distal end of said ETT and said distal end of said introducer and forming a combined introducer-ETT unit having a shrouded combined distal end;

f. lubricating a region between said shroud of said introducer and said distal end of said ETT with surgical lubricant to prevent sticking during subsequent withdrawal of said introducer from said lumen of said ETT;

g. inserting a tube exchanger into an in-place ETT within a patient's airway to serve as a guide wire for its removal;

h. withdrawing said in-place ETT over said tube exchanger;

i. advancing said combined introducer-ETT unit over said tube exchanger so as to place said shrouded combined distal end of said combined introducer-ETT unit between and beyond said patient's vocal cords;

j. removing said surgical tape or said fixation ring and withdrawing said introducer from said ETT, leaving said ETT properly positioned in said patient's trachea.

* * * * *